(12) United States Patent
Jonkman

(10) Patent No.: US 6,530,902 B1
(45) Date of Patent: Mar. 11, 2003

(54) CANNULA PLACEMENT SYSTEM

(75) Inventor: Kenneth R. Jonkman, Grand Rapids, MI (US)

(73) Assignee: Medtronic, Inc., Minneapolis, MN (US)

( * ) Notice: Subject to any disclaimer, the term of this patent is extended or adjusted under 35 U.S.C. 154(b) by 248 days.

(21) Appl. No.: 09/012,530

(22) Filed: Jan. 23, 1998

(51) Int. Cl.7 ................................................ A61M 5/00
(52) U.S. Cl. ........................................................ 604/164
(58) Field of Search .............................. 604/158, 161, 604/164, 166, 264, 280

(56) References Cited

U.S. PATENT DOCUMENTS

| | | | |
|---|---|---|---|
| 3,946,741 A | * 3/1976 | Adair | 604/164 |
| 4,629,450 A | 12/1986 | Suzuki et al. | |
| 4,978,334 A | * 12/1990 | Toye et al. | 604/51 |
| 4,995,866 A | 2/1991 | Amplatz et al. | |
| 5,057,083 A | 10/1991 | Gellman | |
| 5,059,183 A | * 10/1991 | Semrad | 604/158 |
| 5,098,393 A | * 3/1992 | Amplaz et al. | 604/167 |
| 5,190,528 A | 3/1993 | Fonger et al. | |
| 5,858,002 A | * 1/1999 | Jesch | 604/158 |

FOREIGN PATENT DOCUMENTS

EP 0232994 8/1987

* cited by examiner

*Primary Examiner*—Brian L. Casler
(74) *Attorney, Agent, or Firm*—Foley & Lardner

(57) ABSTRACT

A cannula assembly for insertion in a blood vessel includes a cannula and a dilator. The cannula has a proximal end, a distal end, and a lumen extending therebetween. The dilator, which is telescopically received in the lumen of the cannula, includes proximal and distal ends, a passage extending between the proximal and distal ends, and a dilator tip disposed at the distal end. The cannula assembly further includes a needle and a guide wire disposed within the passage of the dilator. The dilator tip has an opening formed therein for receiving one of the needle and guide wire. The dilator tip is configured to limit insertion of the needle in the blood vessel.

5 Claims, 6 Drawing Sheets

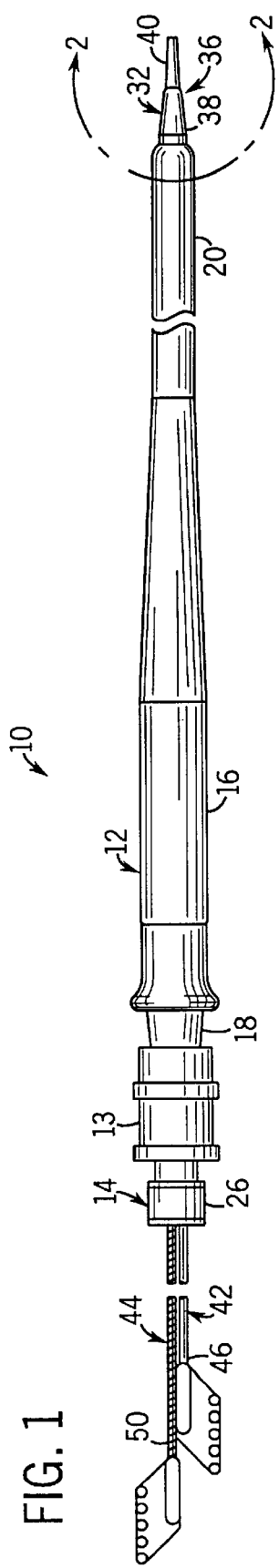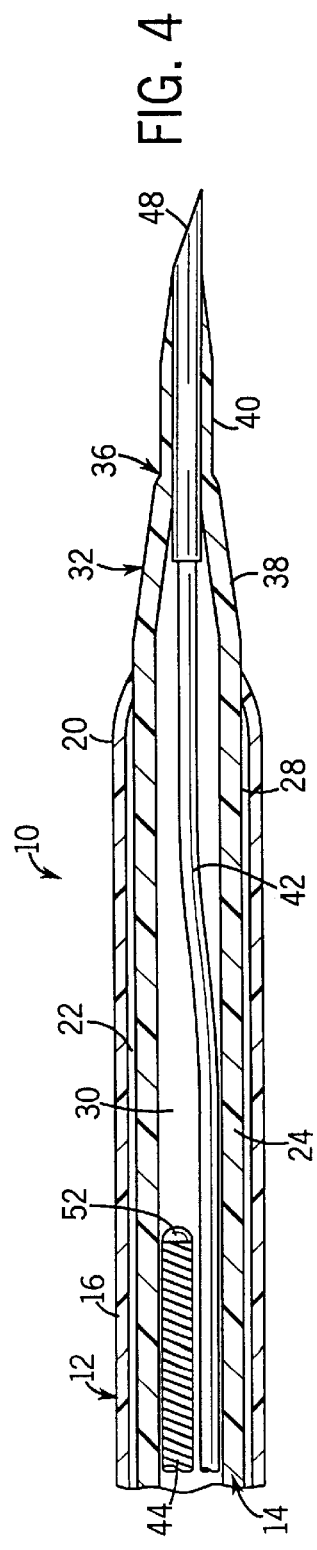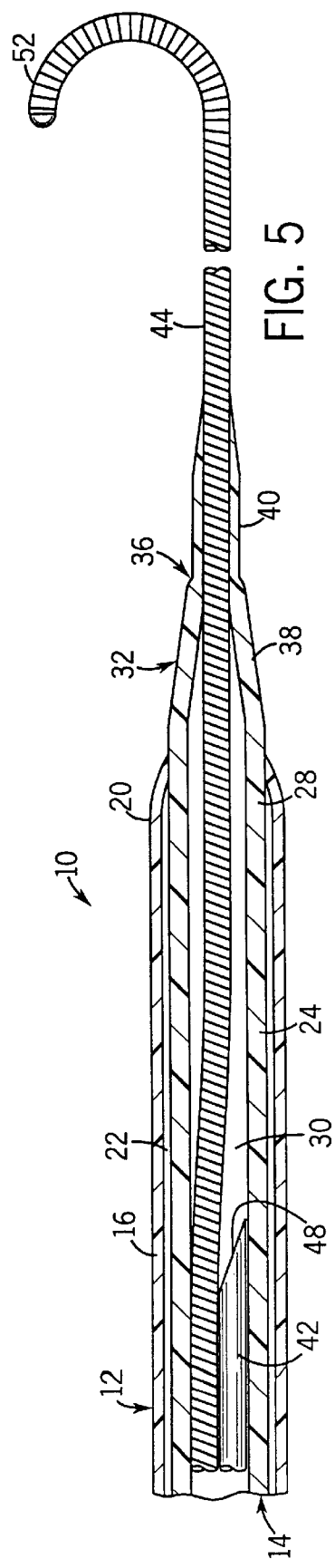

CANNULA PLACEMENT SYSTEM

BACKGROUND OF THE INVENTION

1. Field of the Invention

The present invention relates to cannulas. More particularly, the present invention relates to a cannula assembly for safely puncturing a blood vessel and introducing a cannula to the puncture site.

2. Description of the Related Art

Cannulas have a wide variety of applications during surgical procedures. For example, in cardiac surgery, venous and arterial cannulas are used to conduct blood between the body and bypass equipment. Cannulas are used to conduct cardioplegia solution for both antigrade and retrograde solution administration, and cannulas are also used as vents, sumps, and for chest tube fluid suction. The structure for these known cannulas generally comprises a cannula body which is circular in cross-section and has at least one lumen extending therethrough which is similarly circular in cross-section. Examples of these structures are seen in U.S. Pat. Nos. 4,639,252, 4,129,129 and 5,395,330.

A conventional method of inserting a cannula into a body includes the steps of placing a purse string suture in the wall of a blood vessel and using a blade to puncture the center of the purse string suture. The blade is then removed, and a finger is used to cover the puncture site to prevent the loss of blood. As the finger is removed from the puncture site, the cannula is simultaneously inserted therein. One problem with this method of cannula insertion is that in many instances, such as in mini-sternotomy and minimally invasive cardiac surgery where the size of the access apertures formed in the chest cavity is minimized, it may be difficult or impossible to access and cover the puncture site with a finger, thereby resulting in a loss of blood. Another problem with this method is the difficulty in controlling the depth to which the blade or needle is inserted in the blood vessel. As a result, there is a risk that the blade or needle may be inserted too far and damage or puncture the back wall of the vessel.

One attempt to address the former problem provides a cannula that may be placed over a guide wire. To insert this cannula into a blood vessel, the center of a purse string suture is punctured with the distal end of a Selginger needle having a stylet disposed therein. Once the needle is inserted, the stylet is removed, and a finger covers the distal end of the needle to minimize blood loss. Next, the finger is removed, and a guide wire is advanced through the needle and into the blood vessel. When the guide wire is situated in the blood vessel, the needle is removed, and a dilator and cannula are placed over the guide wire. The dilator and cannula are inserted in the blood vessel until the cannula is in the desired position, at which point the dilator and guide wire are removed. While this approach eliminates the need for a finger covering the puncture site and reduces blood loss at the site, there is still blood loss at the proximal end of the needle, which must be covered by a finger during insertion of the cannula. In addition, there is no regulation of the insertion depth of the needle for preventing damage to the blood vessel.

SUMMARY OF THE INVENTION

The cannula assembly according to the invention overcomes the problems of the prior art by providing a cannula assembly including a cannula with a dilator, needle and guide wire disposed therein. In addition, the dilator of the cannula assembly includes dilator tip which is configured to limit insertion of the needle. Thus, the present invention provides a cannula assembly that safely punctures a blood vessel, dilates the puncture site and guides a cannula into place in the vessel.

In accordance with one embodiment of the invention, a cannula assembly is provided for insertion in a blood vessel. The cannula assembly includes a cannula and a dilator. The cannula has proximal and distal ends, and a lumen extending between the proximal and distal ends. The dilator, which is telescopically received in the lumen of the cannula, includes proximal and distal ends and a passage extending therebetween. The cannula assembly further includes a needle and a guide wire disposed, adjacent one another, within the passage of the dilator. The dilator includes a dilator tip which is configured to limit insertion of the needle in the blood vessel.

In another embodiment of the invention, a dilator is provided for a cannula assembly. The dilator includes an elongate tube having proximal and distal ends and a passage formed therein. The passage is adapted to receive simultaneously a needle and a guide wire. The dilator also includes a dilator tip coupled to the distal end of the elongate tube. The dilator tip has an opening formed therein and is configured to limit insertion of the needle.

The invention is also directed to a method of inserting a cannula in a blood vessel. The method includes the step of providing a cannula assembly including a cannula, dilator, needle and guide wire, as described above. The cannula assembly is advanced, with the needle extended through the opening of the dilator tip, a predetermined distance through the outer wall of the blood vessel, thereby forming an incision in the blood vessel. The needle is then retracted from the dilator tip, and the guide wire is extended through the opening of the dilator tip and into the incision. Next, the dilator and cannula are advanced over the guide wire and into the incision. Finally, the dilator, needle and guide wire are removed from the cannula.

Other advantages of the invention will become apparent from the detailed description given hereinafter. It should be understood, however, that the detailed description and specific embodiment are given by way of illustration only, since, from this detailed description, various changes and modifications within the spirit and scope of the invention will become apparent to those skilled in the art.

BRIEF DESCRIPTION OF THE DRAWINGS

The invention will now be described with reference to the drawings in which:

FIG. 1 is a top plan view of a cannula assembly, according to the present invention, including a cannula, dilator, needle and guide wire;

FIG. 4 is a cross-sectional view of the distal end showing the needle extended and the guide wire retracted;

FIG. 5 is a cross-sectional view of the distal end showing the needle retracted and the guide wire extended;

DETAILED DESCRIPTION OF THE PREFERRED EMBODIMENT

Figure 2:
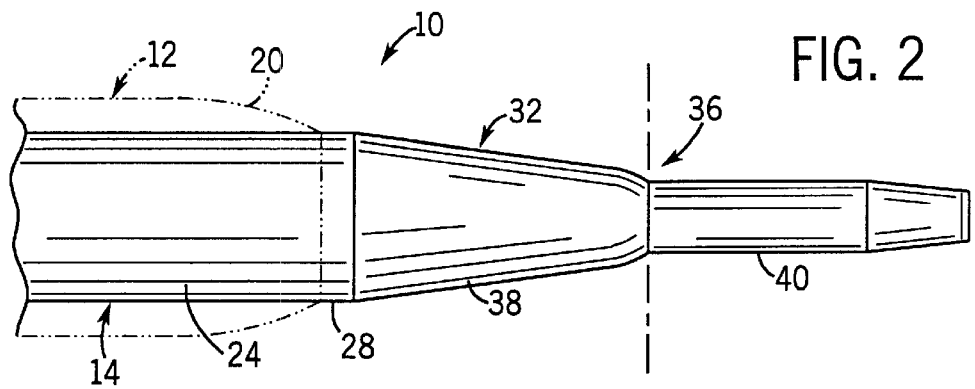
FIG. 2 is a sectional view of the distal end of the cannula assembly taken generally about the arc 2—2 of FIG. 1.

Referring now to the drawings and to FIGS. 1–7 in particular, a preferred embodiment of a cannula assembly 10 according to invention is shown. The cannula assembly 10 includes a cannula 12 and a dilator 14 which is selectively and telescopically received in the cannula 12. The cannula 12 is similar to the cannula described in U.S. Pat. No. 5,190,528, which is expressly incorporated herein by reference. The cannula 12 includes a cannula body 16 having a proximal end 18, a distal end 20, and a lumen 22 extending between the proximal and distal ends.

Figure 3:
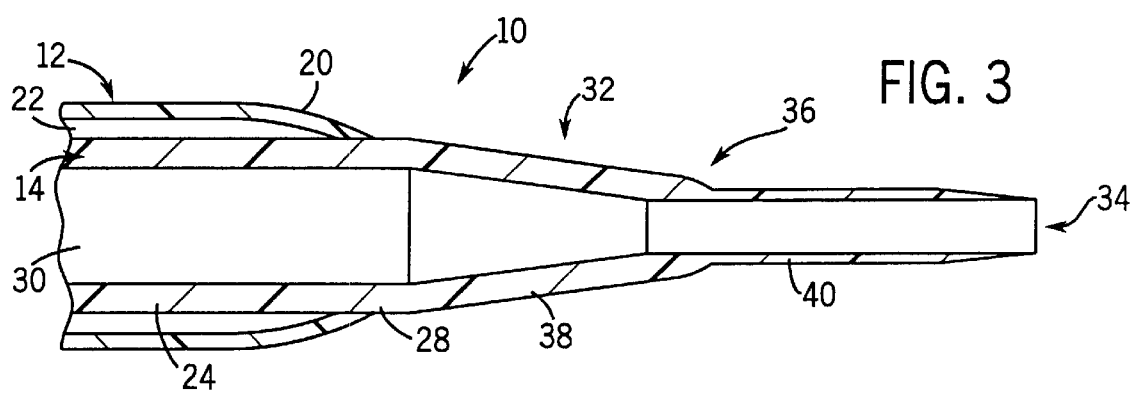
FIG. 3 is a cross-sectional view of the distal end shown in FIG. 2.
Figure 6:
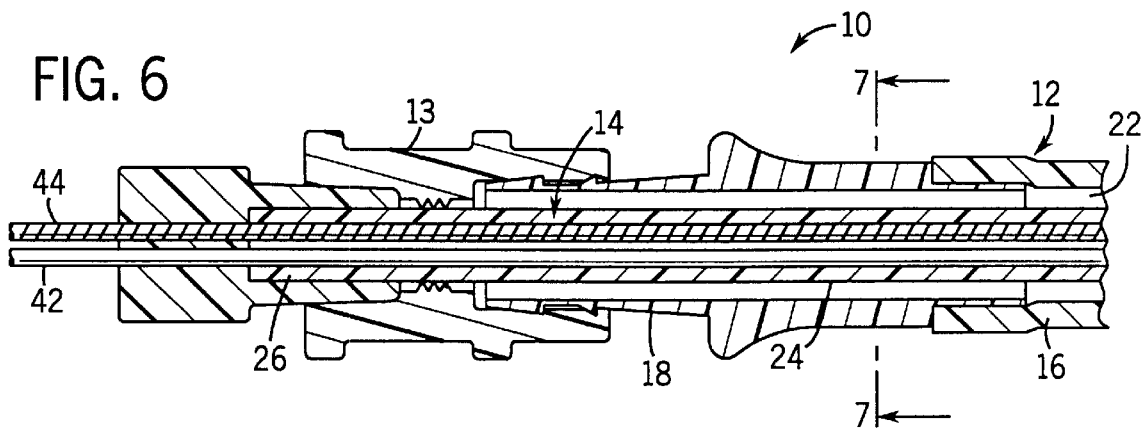
FIG. 6 is a cross-sectional view of the proximal end of the cannula assembly of FIG. 1.

The dilator 14, which is received in the lumen 22 of the cannula 12, includes an elongate tube 24 having a proximal end 26, a distal end 28 and a passage 30 extending between the proximal and distal ends. The dilator 14 is inserted into the lumen 22 at the proximal end 18 of the cannula 12 and, when fully inserted, extends from the distal end 20 thereof. As best illustrated in FIG. 3, the dilator 14 substantially fills the lumen 22 at the distal end 20 of the cannula 12. A flow guard 13 couples the proximal end 18 of the cannula 12 to the dilator 14 to prevent fluid from escaping through the proximal end during insertion of the cannula assembly 10.

The dilator 14 further includes a dilator tip 32, which is coupled to the distal end 28 of the elongate tube 24. Preferably, the dilator tip 32 is integrally formed with the elongate tube 24. However, one skilled in the art will appreciate that the dilator tip 32 may otherwise be coupled to the elongate tube 24 in a conventional manner. The dilator tip 32 extends from the distal end 20 of the cannula 12, when the dilator 14 is fully inserted, and has an opening 34 formed therein. The dilator tip 32 is configured such that the dilator tip 32 temporarily stops the insertion of the dilator 14 into an incision or puncture site. In the preferred embodiment of the invention, this is achieved by providing a transition stop 36 on the dilator tip 32. The transition stop 36 is disposed between a first, tapered portion 38 and a second, generally cylindrical portion 40 of the dilator tip 32. It should be noted that other configurations of the dilator tip 32 may provide the same function. This advantageous feature of the dilator tip 32 will be described in greater detail below.

Figure 7:
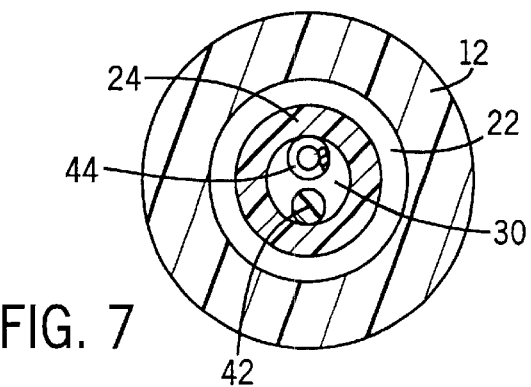
FIG. 7 is a cross-sectional view taken generally along the line 7—7 of FIG. 6.

The cannula assembly 10 further includes a needle 42 and a guide wire 44. As best illustrated in FIG. 7, the needle 42 and guide wire 44 are axially disposed adjacent one another in the passage 30 of the elongate tube 24 of the dilator 14. The needle 42 is provided to pierce the wall of a blood vessel so that cannula assembly 10 may be inserted. The needle 42 has a proximal end 46 and a distal end 48. When the needle 42 is fully inserted into the cannula assembly 10, as shown in FIG. 4, the distal end 48 extends from the dilator tip 32 by a predetermined distance. Accordingly, the depth to which the needle 42 is inserted in a blood vessel is determined by the depth to which the cannula assembly 10, with the needle 42 extended, is inserted prior to retraction of the needle 42. The needle is of sufficient length such that, when the cannula assembly 10 with the needle 42 extended is inserted in a blood vessel of a body, the needle 42 may still be manipulated via its proximal end 46.

The guide wire 44, which is disposed in the passage 30 with the needle 42, directs the cannula assembly 10 through the blood vessel. The guide wire 44 includes a proximal end 50 and a distal end 52. As shown in FIG. 5, when the distal end 52 of the guide wire 44 is extended through the dilator tip 32, the guide wire 44 assumes a curled configuration, which facilitates direction of the cannula assembly 10 through the blood vessel. Like the needle 42, the length of the guide wire 44 is long enough that its proximal end 50 may be manipulated even when the distal end 52 is inserted in the blood vessel.

Although the needle 42 and guide wire 44 are both disposed in the passage 30 of the elongate tube 24, the opening 34 in the dilator tip 32 is large enough to accommodate only one of the needle 42 and guide wire 44 at a time, and each substantially fills the opening 34. As illustrated respectively in FIGS. 4 and 5, either the needle 42 or the guide wire 44 may be extended, with the other retracted in passage 30 of the elongate tube 24.

Figure 8:
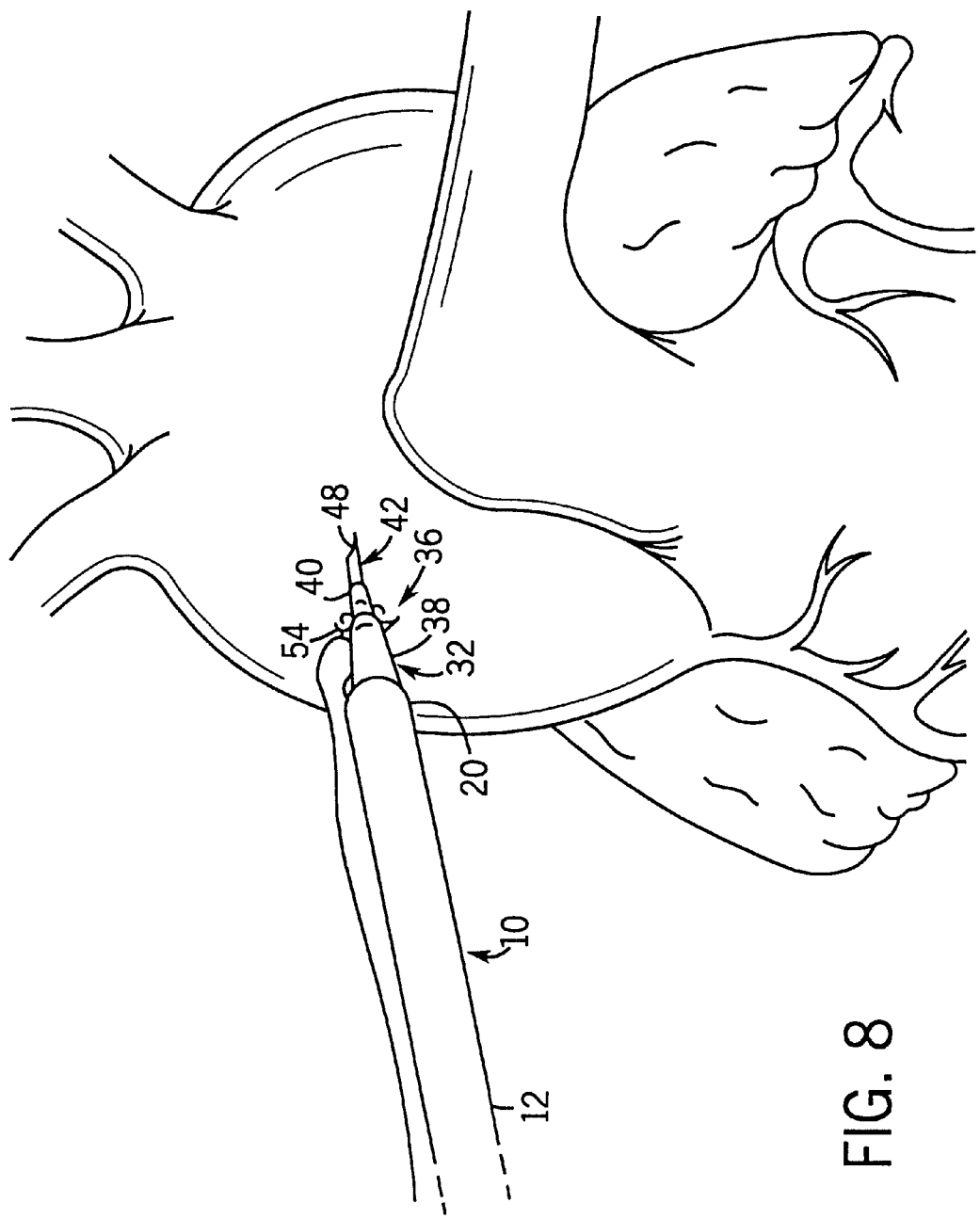
FIG. 8 is a schematic view of the cannula assembly, with the needle extended, showing the needle and dilator tip positioned in a purse string suture in the aorta of a heart.

Referring now to FIGS. 8–11, the operation of the cannula assembly 10 will be described. The cannula assembly 10 described above is ideally suited for use as an arterial cannula during a cardiac surgical procedure. Prior to the insertion of the cannula assembly in the aorta of a heart, a purse string suture 54 is placed in the wall of the aorta. The cannula assembly 10, with the needle 42 extended through the opening 34 of the dilator tip 32, is advanced to the center of the purse string suture 54. As shown in FIG. 8, the distal end 48 of the needle 42 punctures the aorta, in the center of the purse string suture 54, and the cannula assembly 10 is inserted into the puncture site until the transition stop 36 of the dilator tip 32 contacts the outer wall of the aorta. In the preferred embodiment of the invention, at this stage, only the distal end 48 of the needle 42 and the generally cylindrical portion 40 of the dilator tip 32 are situated in the aorta. By temporarily halting further advancement of the cannula assembly 10 in the aorta, the transition stop 36 is able to control the insertion depth of the needle 42 in the aorta, thereby minimizing the risk of damage to the back wall of the aorta.

Figure 9:
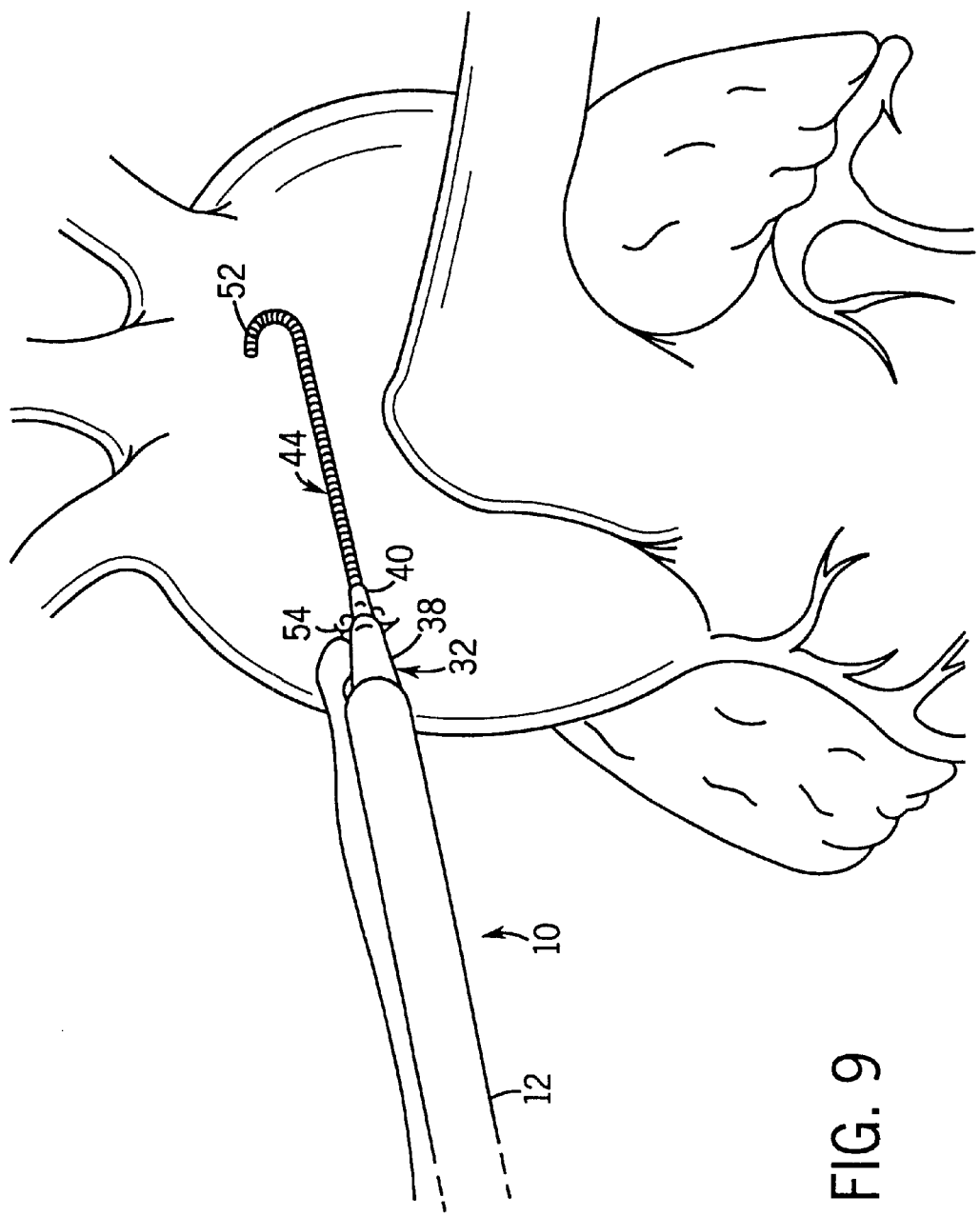
FIG. 9 is a schematic view of the cannula assembly showing the guide wire extended in the aorta.
Figure 10:
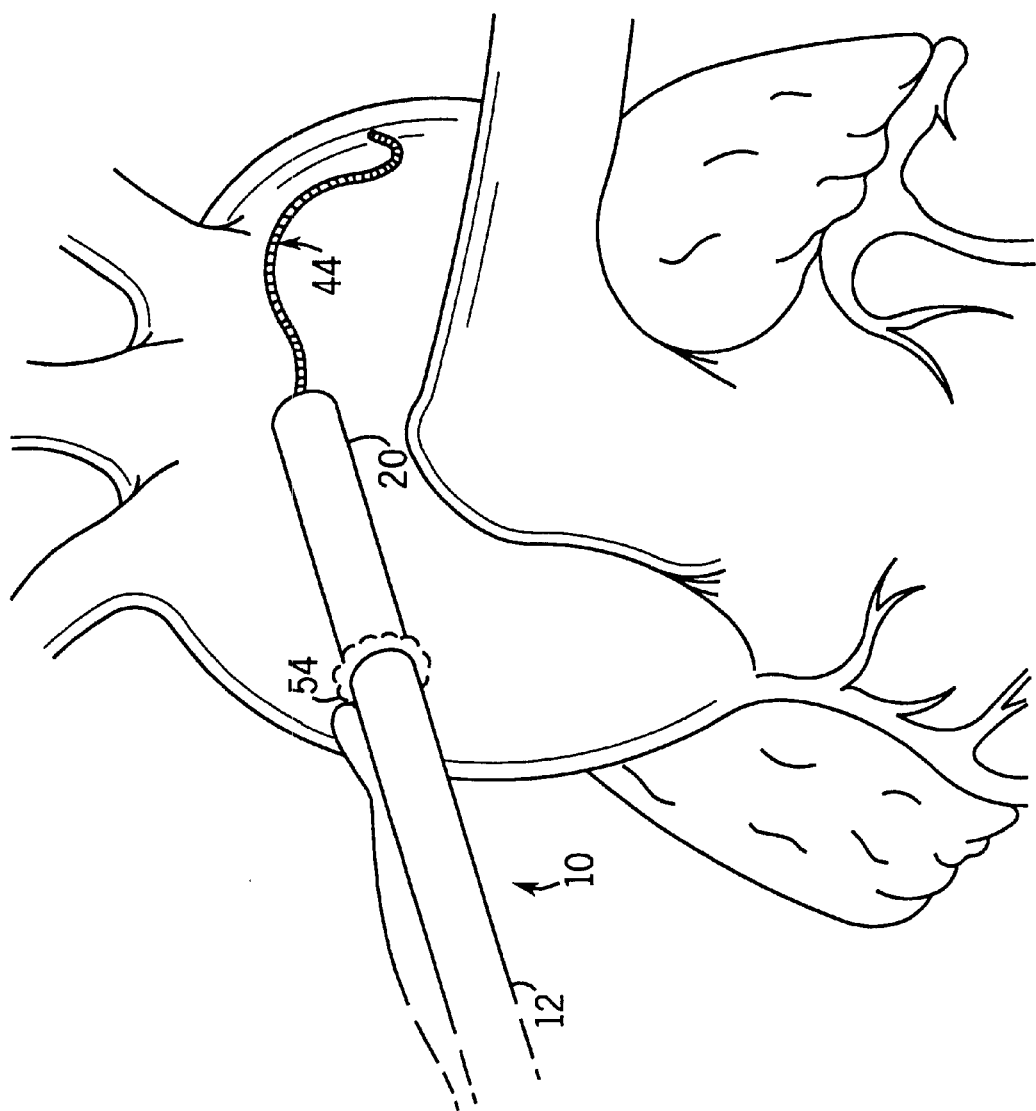
FIG. 10 is a schematic view of the cannula assembly showing the cannula and dilator advanced over the guide wire and inserted in the aorta.
Figure 11:
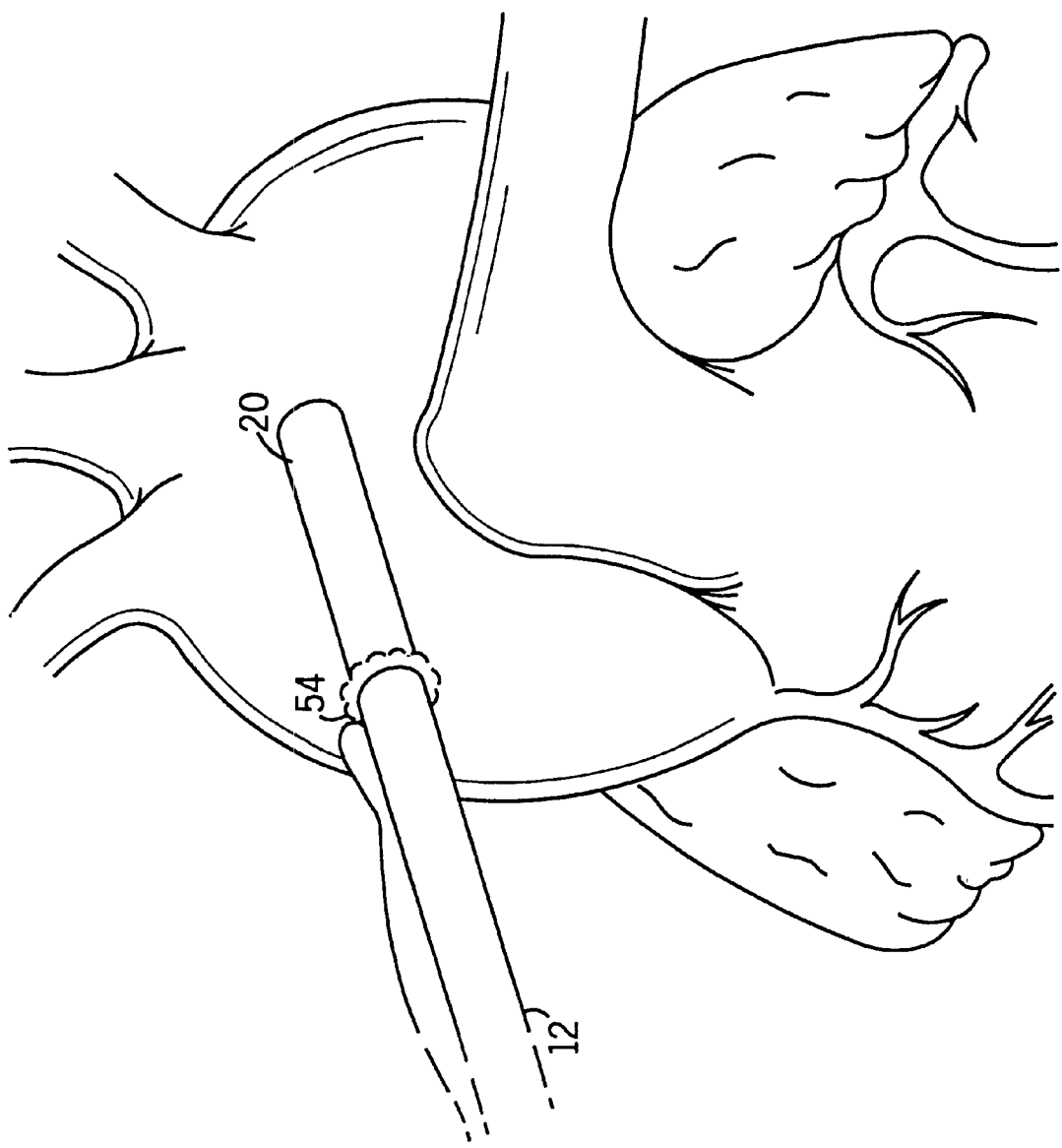
FIG. 11 is a schematic view of the cannula assembly showing the cannula, with the dilator, needle and guide wire removed, positioned in the aorta.

Once the cannula assembly 10 has been inserted in the aorta, up to the transition stop 36, the needle 42 is retracted into the passage 30 of the elongate tube 24, and the guide wire 44 is extended through the opening 34 of the dilator tip 32 and into the aorta (FIG. 9). The guide wire 44 facilitates insertion of the cannula 12 in the aorta. The cannula 12 and dilator 14 are then advanced over the guide wire 44 and into the aorta (FIG. 10). When the cannula 12 is properly positioned in the aorta, the needle 42, dilator 12, and guide wire 44 are withdrawn, leaving the cannula 12 in place. Since the cannula 12, dilator 14, and needle 42 or guide wire 44 fills the puncture site at all times, the cannula assembly 10 of the present invention eliminates the need to cover the puncture site. In addition, the transition stop 36 of the dilator tip 32 reduces the risk that the needle 42 will be inserted too deep and damage the aorta.

While the preferred embodiment of the cannula assembly 10 described above is an arterial cannula, it is to be understood that the invention extends to any cannula inserted into the body through an access aperture.

Reasonable variation and modification are possible within the spirit of the foregoing specification and drawings without departing from the scope of the invention.

What is claimed is:

1. A cannula assembly for insertion in a blood vessel, the cannula assembly comprising:

a cannula having a proximal end, a distal end, and a lumen extending therebetween;

a dilator telescopically received in the lumen of the cannula, the dilator having a proximal end, a distal end, and a passage formed therein, the dilator further including a dilator tip disposed at the distal end;

a guide wire disposed in the passage of the dilator; and a needle located adjacent the guide wire in the passage of the dilator, wherein the dilator tip is configured to limit insertion of the needle in the blood vessel and the dilator being configured to be selectively extended from or retracted into the cannula independent of the guide wire and needle.

2. A cannula assembly according to claim 1, wherein the dilator tip includes a transition stop for limiting insertion of the needle.

3. A cannula assembly according to claim 2, wherein the dilator tip has a tapered portion and a generally cylindrical portion located distally of the tapered portion, the transition stop being disposed between the tapered and generally cylindrical portions.

4. A cannula assembly according to claim 1, wherein the dilator tip has an opening formed therein for receiving one of the needle and the guide wire.

5. A cannula assembly according to claim 1, wherein each of the needle and guide wire is of a sufficient length to extend out of the body for manipulation when either distal end thereof is positioned within the blood vessel.

* * * * *